(12) United States Patent
Sakamoto et al.

(10) Patent No.: US 6,540,881 B1
(45) Date of Patent: Apr. 1, 2003

(54) METHOD FOR REFINING (METH)ACRYLIC ACID

(75) Inventors: Kazuhiko Sakamoto, Himeji (JP); Kouji Ueno, Himeji (JP); Sei Nakahara, Himeji (JP); Masatoshi Ueoka, Himeji (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/532,225

(22) Filed: Mar. 22, 2000

(30) Foreign Application Priority Data

Mar. 31, 1999  (JP) ............................. 11-093859

(51) Int. Cl.⁷ ................ B01D 3/42; C07C 51/44; C07C 51/21
(52) U.S. Cl. .................. 203/3; 203/8; 203/49; 203/71; 203/DIG. 21; 203/9; 562/600
(58) Field of Search ................ 203/7, 1, 2, 80, 203/9, 8, 71, DIG. 21, 100, 3, 49; 562/600, 545, 532, 531

(56) References Cited

U.S. PATENT DOCUMENTS

| 4,021,310 A | | 5/1977 | Shimizu et al. | |
| 4,199,410 A | * | 4/1980 | Ohrui et al. | 203/49 |
| 4,987,252 A | * | 1/1991 | Kuragano et al. | 562/485 |
| 5,770,021 A | * | 6/1998 | Hego et al. | 203/49 |
| 5,855,743 A | | 1/1999 | Herbst et al. | 203/74 |

FOREIGN PATENT DOCUMENTS

| EP | 0648 732 A | 4/1995 |
| EP | 0 695 736 A1 | 7/1996 |
| GB | 1127127 | 9/1968 |
| JP | A-51-98211 | 8/1976 |
| JP | A-7-149687 | 6/1995 |

* cited by examiner

*Primary Examiner*—Virginia Manoharan
(74) *Attorney, Agent, or Firm*—Mathews, Collins, Shepherd & McKay, P.A.

(57) ABSTRACT

This invention relates to a method for preventing (meth) acrylic acid from polymerizing during the course of distillation. The method provides for refining (meth)acrylic acid by a procedure including the steps of feeding a mixed gas obtained by catalytic gas phase oxidation of propylene and/or acrolein with a molecular oxygen-containing gas or a mixed gas obtained by catalytic gas phase oxidation of at least one compound of isobutylene, t-butyl alcohol, or methacrolein with a molecular oxygen-containing gas, to a (meth)acrylic acid collection column, collecting a (meth) acrylic acid-containing solution from the mixed gas, and feeding the (meth)acrylic acid-containing solution to a distillation column while maintaining the total concentration of aldehydes of 2–4 carbon atoms and acetone in the solution at a level of not more than 2000 ppm based on the amount of (meth)acrylic acid.

15 Claims, 1 Drawing Sheet

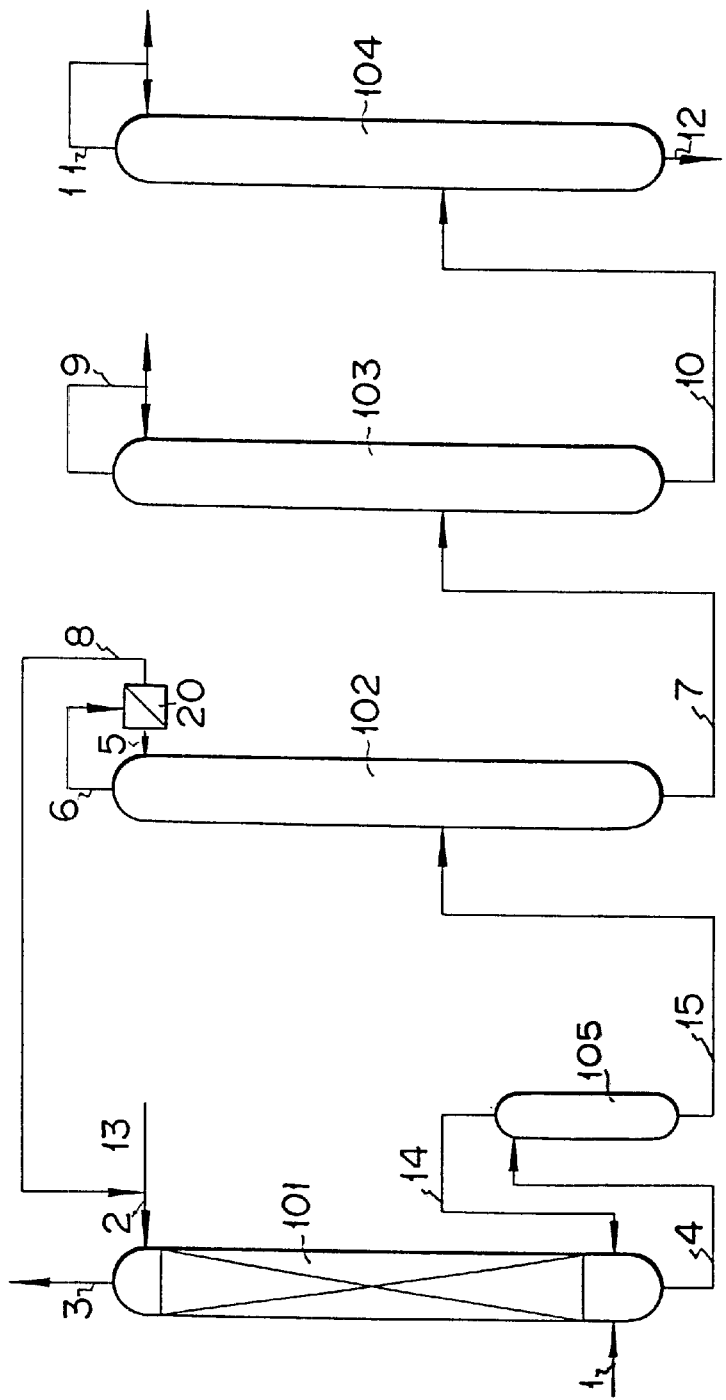

METHOD FOR REFINING (METH)ACRYLIC ACID

BACKGROUND OF THE INVENTION

1. Field of the Invention

This invention relates to a method for effectively preventing (meth) acrylic acid from polymerizing during the course of distillation.

2. Description of the Related Art

It is generally known that acrylic acid has a nature to easily and spontaneously polymerize on exposure to light and heat. During the production of acrylic acid, therefore, various polymerization inhibitors such as hydroquinone, methoquinone, phenothiazine, copper dibutyl dithiocarbamate, p-phenylene diamines, and N-oxyl compounds are added either singly or in the form of a combination of two or more members to the reaction system of production with the object of preventing acrylic acid from polymerizing.

U.S. Pat. No. 4,021,310 discloses a method for preventing acrylic acid from polymerizing by using a polymerization inhibitor composed of at least one compound selected from the group consisting of hydroquinone, methoquinone, cresol, phenol, t-butyl catechol, diphenyl amine, phenothiazine, and methylene blue, at least one compound selected from the group consisting of copper dimethyl dithiocarbamate, copper diethyl dithiocarbamate, copper dibutyl dithiocarbamate, and copper salicylate, and molecular oxygen.

JP-A-51-98,211 discloses a method for preventing acrylic acid from polymerizing by using a polymerization inhibitor composed of a manganese salt such as manganese acetate, hydroquinone and/or methoquinone, and molecular oxygen.

GB 1127127 discloses a method for preventing acrylic acid from polymerizing by using a N-oxyl compound such as tertiary butyl nitroxide or 4-hydroxy-2,2,6,6-tetramethyl piperidinoxyl.

Then, EP 695736 discloses a method for refining acrylic acid by distilling in an azeotropic dehydration distillation column an aqueous acrylic acid solution obtained by absorbing in water the reaction gas resulting from oxidizing propylene and/or acrolein with a molecular oxygen-containing gas or the liquid resulting from deriving the solution of aldehydes, which method effects the refinement by causing the bottoms of the distillation column to contain an azeotropic solvent at a prescribed concentration and consequently preventing the liquid in the distillation column from polymerizing.

A study made by the present inventors on the methods for preventing acrylic acid from polymerization by using polymerization inhibitors as described above has revealed that these methods fail to manifest a fully satisfactory effect in preventing polymerization under the conditions shown below.

In the production of acrylic acid by catalytic gas phase oxidation of propylene and/or acrolein with a molecular oxygen-containing gas, the acrylic acid-containing solution which occurs therein is distilled in a distillation column. Since this acrylic acid-containing solution is so composed as to contain impurities such as water, acetic acid, and acrolein, it is highly liable to induce polymerization of acrylic acid. When such a polymerization inhibitor as mentioned above is used at an ordinary application rate, it fails to produce a fully satisfactory effect in preventing polymerization. The solution during the course of distillation, therefore, is suffered to give rise to a polymer and the polymer renders protracted continuous operation of the distillation column difficult. In order for the continuous operation to last, it becomes necessary to use the polymerization inhibitor in a large amount. Thus, the polymerization inhibitor has not been fit for use in an actual apparatus.

The effect of preventing polymerization which is recited in EP 695736 is attained by causing bottoms in the azeotropic dehydration distillation column to allow presence of an azeotropic solvent at a prescribed concentration. Nowhere in this publication is found any mention purporting that the presence or absence of aldehydes in the aqueous acrylic acid solution supplied to the distillation column mentioned above affects the liability of this solution to polymerization during the course of distillation. In the examples cited therein, the distillation was performed only on aqueous acrylic acid solutions containing 0.3 wt. % of formaldehyde. The liability to polymerization of an aqueous acrylic acid solution containing a specific aldehyde at a specific concentration is mentioned nowhere.

The same problems are also encountered in the refinement of methacrylic acid.

SUMMARY OF THE INVENTION

The aforementioned prior patent publications disclosing methods for preventing acrylic acid from polymerization have absolutely no mention of the relation between the concentration of a specific aldehyde or ketone in the acrylic acid-containing solution fed into the distillation column and the effect of a polymerization inhibitor.

The present inventors have ascertained by their own study that the expected effect of preventing polymerization is not attained fully satisfactorily, depending on the concentration of a specific aldehyde or ketone in the acrylic acid-containing solution fed into the distillation column.

Thus, it is an object of this invention to provide a method for effectively preventing (meth) acrylic acid in a (meth) acrylic acid-containing solution from polymerizing during the distillation of the solution by the use of a polymerization inhibitor.

The present inventors have pursued studies on the prevention of acrylic acid in an acrylic acid-containing solution obtained by catalytic gas phase oxidation of propylene and/or acrolein from polymerizing during the distillation of the solution and, consequently, have found that the prevention of acrylic acid from polymerization is effectively attained by maintaining the total concentration of aldehydes of 2 to 4 carbon atoms and acetone in the acrylic acid-containing solution fed into a distillation column below a prescribed level. This invention has been achieved based on this knowledge. They have further found that this knowledge is applicable to the refinement of methacrylic acid.

To be specific, according to this invention it can provide a method for refining (meth) acrylic acid by a procedure comprising the steps of feeding a mixed gas obtained by catalytic gas phase oxidation of propylene and/or acrolein with a molecular oxygen-containing gas or a mixed gas obtained by catalytic gas phase oxidation of at least one compound selected from the group consisting of isobutylene, t-butyl alcohol, and methacrolein with a molecular oxygen-containing gas to a (meth)acrylic acid collection column, collecting a (meth)acrylic acid-containing solution from the mixed gas, feeding the (meth) acrylic acid-containing solution to a distillation column, and separating and recovering (meth) acrylic acid from the solution, which method is characterized by feeding the (meth)acrylic acid-containing solution to the distillation column while maintaining the total concentration of aldehydes of 2–4 carbon atoms and acetone in the solution at a level of not more than 2000 ppm based on the amount of (meth)acrylic acid.

The above and other objects, features, and advantages of the present invention will become clear from the following description of the preferred embodiment.

BRIEF DESCRIPTION OF THE DRAWING

FIGURE is a process diagram illustrating one method of this invention which comprises collecting acrylic acid formed in advance and then refining the collected acrylic acid.

DESCRIPTION OF THE PREFERRED EMBODIMENTS

Now, this invention will be described below using acrylic acid as the representative.

The catalytic gas phase oxidation reaction of this invention is not limited particularly on account of the kind of first-stage catalyst and second-stage catalyst. These two catalysts can be effectively used so long as the first-stage catalyst is capable of chiefly forming acrolein by the gas phase oxidation of propylene and the second-stage catalyst is capable of chiefly forming acrylic acid by the gas phase oxidation of acrolein. Examples of the first-stage catalyst may include complex oxides containing iron, molybdenum, and bismuth. Examples of the second-stage catalyst may include catalysts having vanadium as an essential component. The first-stage catalysts and the second-stage catalysts of this invention, therefore, embrace respectively the so-called first-stage catalysts and second-stage catalysts which are generally used at present in the first step and the second step in the production of acrylic acid by the two-stage reaction method (JP-B-60-32,615).

The methods for preparing these catalysts are not particularly limited, but can be selected from which are generally known in the art.

The kind and the method of use of the reaction vessel and the thermal medium to be used in this invention is not particularly limited. The reaction vessels that can be used herein may include the reaction vessels of the shell-and-tube heat exchanger type, of the fluidized bed type, and of the moving bed type (JP-B-60-29,290).

This invention, in a process comprising the steps of feeding a mixed gas obtained by catalytic gas phase oxidation of propylene and/or acrolein with a molecular oxygen-containing gas to an acrylic acid collection column, collecting an acrylic acid-containing solution from the mixed gas, feeding this acrylic acid-containing solution to a distillation column, and separating and recovering acrylic acid from the solution, is characterized by feeding the acrylic acid-containing solution into the distillation column while maintaining the total concentration of aldehydes of 2–4 carbon atoms and acetone (specific impurities) in the acrylic acid-containing solution at a level of not more than 2000 ppm based on the amount of acrylic acid in the solution, preferably the concentration of (meth)acrolein in the acrylic acid-containing solution at a level of not more than 100 ppm, more preferably at a level of not more than 50 ppm, based on the amount of acrylic acid. Examples of the aldehydes of 2–4 carbon atoms may include (meth)acrolein, acetaldehyde, and glyoxal.

The acrylic acid-containing solution contains impurities such as aldehydes, acetone, water, acetic acid, formic acid and maleic acid.

The method for decreasing the content of aldehydes of 2–4 carbon atoms and acetone in this invention is not particularly limited. For the purpose of this decrease, any of the heretofore known methods may be adopted. Examples of the method which is used effectively for effecting this decrease may include a method which consists in increasing the rate of conversion of acrolein in the reaction of catalytic gas phase oxidation, a method which consists in decreasing the concentration of the aforementioned compounds contained in the acrylic acid-containing solution by elevating the temperature of collection in the acrylic acid collecting column, and a method which consists in adding a step of feeding the acrylic acid-containing solution into a stripping column may be cited. Among other methods mentioned above, the method which resides in adding the step of feeding the acrylic acid-containing solution into the stripping column proves particularly advantageous from the viewpoint of the ease with which the concentration of the compounds mentioned above is adjusted.

Generally, a distillation column or tower is adopted as the stripping column which fits the intended use in this invention. The operating conditions for the distillation column have no particular restriction but are only required to set the total concentration of aldehydes of 2–4 carbon atoms and acetone in the acrylic acid-containing solution at a level of not more than 2000 ppm, preferably at a level of not more than 100 ppm, more preferably at a level of not more at than 50 ppm, based on the amount of acrylic acid. Examples of the distillation column that is used effectively herein may include a packed column, a plate tower (tray power), a wet wall column, and a spray column. The operating conditions have no particular restriction but are only required to permit expected refinement of acrylic acid. Generally, the operating pressure may be in the range of 100–700 h Pa, the column top temperature in the range of 50–100° C., and the column bottom temperature in the range of 50–100° C.

The polymerization inhibitor to be used in the distillation column is not particularly limited. Any of the compounds that are generally accepted as a polymerization inhibitor for acrylic acid can be used. Examples of the compound which is advantageously used herein may include hydroquinone, methoquinone, and phenothiazine; a copper salt compound such as copper dimethyl dithiocarbamate, copper diethyl dithiocarbamate, copper dibutyl dithiocarbamate, and copper salicylate; a manganese salt compound such as manganese acetate; a p-phenylene diamine compound such as p-phenylene diamine, a N-oxyl compound such as 4-hydroxy-2,2,6,6-tetramethyl piperidinoxyl; a nitroso compound such as N-nitrosodiphenyl amine; an urea compound such as urea, a thiourea compound such as a thiourea and the like. The compounds mentioned above may be used either singly or in the form of a combination of two or more members. Among other compounds enumerated above, phenothiazine and/or a N-oxyl compound proves particularly proper from the viewpoint of affording effective prevention of polymerization, enabling the distillation column to resist corrosion, and permitting the effluent from the distillation column to be easily treated for disposal.

The method for adding to the distillation column the polymerization inhibitor to be used at the distillation step for feeding the acrylic acid-containing solution has no particular restriction. This polymerization inhibitor may be directly fed into the distillation column or it may be dissolved in a feed solution, a reflux liquid, or other solvent and then fed in the form of the resultant solution to the distillation column via the feed line. The amount of the polymerization inhibitor to be used is not particularly restricted. The total amount of the polymerization inhibitor, however, may fall in the range of 1–1000 ppm (by weight), especially in the range of 5–500 ppm, based on the amount of the vapor of acrylic acid. The term "amount of vapor" as used herein means the total amount of the vapor of the monomer which boils up from the bottom of the column in proportion to the quantity of heat added from the re-boiler of the distillation column.

The expression "distillation column to be utilized for this invention" as used herein means all the distillation columns that participate in the refining step for feeding the acrylic acid-containing solution. These distillation columns serve the purpose of recovering the acrylic acid from a mixture of the solvent with acrylic acid, obtained by cooling and washing in counter flow with a solvent the acrylic acid-containing gas resulting from catalytic gas phase oxidation of propylene and/or acrolein. Examples of the distillation column may be cited a solvent separation column, an azeotropic separation column, an acetic acid separation column, and a high boiling component separation column, in particular with a multistage.

FIGURE is a process diagram illustrating one example of a method which comprises collecting the formed acrylic acid and subsequently refining the acrylic acid. With reference to FIGURE, the acrylic acid-containing gas obtained by catalytic gas phase oxidation of a feed gas containing propylene and/or acrolein with a molecular oxygen-containing gas is fed via a line (conduit) 1 into an acrylic acid collection column 101 and caused therein to contact the water fed via a line 2, with the result that an aqueous acrylic acid solution containing acrylic acid and by-products such as acetic acid will be obtained via a line 4. As the water to be supplied via the line 2 to the acrylic acid collection column 101, though the water supplied via a line 13 may be used, it is proper to use the water phase in a storage tank 20 which will be described more specifically below. The aqueous acrylic acid solution is fed into a stripping column 105 and caused therein to strip aldehydes and acetone dissolved therein and thereafter fed into an azeotropic separation column 102. The term "stripping" as used herein refers to an operation of expelling lighter components than acrylic acid generally by the use of a distillation column. The conditions for the stripping have no particular restriction but are for example only required to induce dissipation of aldehydes and acetone. Generally, the operating pressure may be in the range of 100–700 h Pa, the column top temperature in the range of 50–100° C., and the bottom temperature in the range of 50–100° C. Preferably in this case, the stripped gas is recovered and circulated via a line 14 to the acrylic acid collection column 101. In the azeotropic separation column 102, the aqueous acrylic acid solution which is received via a line 15 and azeotropic solvents such as toluene which are received via a line 5 are distilled, with the result that an azeotropic mixture composed of water and the azeotropic solvent will be distilled via the top of the column and acrylic acid containing acetic acid will be obtained via the bottom of the column. An azeotropic mixture composed of water and the azeotropic solvent is distilled via the top of the azeotropic separation column 102 and fed into the storage tank 20, wherein an organic phase formed mainly of the azeotropic solvent and a water phase formed mainly of water will be separated. The organic phase is circulated via the line 5 to the azeotropic separation column 102. Meanwhile, the water phase is circulated via a line 8 to the acrylic acid collection column 101 and can be effectively utilized as the collecting water for contact with the acrylic acid-containing gas brought in via the line 1. The acrylic acid which has been extracted from the azeotropic separation column 102 through the bottom thereof is fed via a line 7 into an acetic acid separation column 103, wherein the acetic acid is separated and removed through the top and the acrylic acid containing substantially no acetic acid is obtained through the bottom. The refined acrylic acid possesses high purity and, therefore, can be directly used as the raw material for the production of an acrylic ester. Naturally, this acrylic acid of high purity may be further fed via a line 10 into a high boiling component separation column 104 to separate and remove a high boiling component and obtain acrylic acid of still higher purity through the top of the column.

The position at which the stripping column is installed is not particularly limited. The stripping column, optionally for the purpose of removing specific impurities, may be interposed between the azeotropic separation column and the low boiling component separation column or between the low boiling component separation column and the high boiling component separation column.

Reference Numeral 3 in Figure represents a line for recycling the gas remaining after the collection of acrylic acid from the acrylic acid-containing gas to the step for the reaction of oxidation. Part of this residual gas is passed through the step for combustion and then discharged as waste gas. Reference Numeral 6 represents a distillation line of the azeotropic separation column 102, Reference Numeral 9 a distillation line of the low boiling component separation column 103, and Reference Numerals 11 and 12 respectively represent a distillation line and a bottoms extraction line of the high boiling component separation column 104.

The method of this invention permits simultaneous use of a molecular oxygen at the distillation step for feeding the acrylic acid-containing solution and consequently allows more effective prevention of acrylic acid from polymerization. As respects the method for supplying a molecular oxygen, the molecular oxygen may be directly mixed with the acrylic acid-containing solution as by bubbling or it may be dissolved in advance in a solvent and the resultant solution used for indirect mixture. The bubbling may be easily accomplished by supplying the molecular oxygen in a gaseous state through the bottom of the distillation column and/or through the re-boiler. Properly, the molecular oxygen may be generally supplied at a rate in the range of 0.1–1 vol. %, preferably 0.2–0.5 vol. %, based on the amount of the vapor of acrylic acid in the distillation column.

Though the case of using methacrylic acid and the case of using acrylic acid have many points in common, they are different in the following points.

For example, they differ in the point that the methacrylic acid-containing solution is fed to the extraction step to effect extraction of methacrylic acid from the methacrylic acid-containing solution through the medium of a solvent before the methacrylic acid-containing solution is fed to the distillation column. Even in this case, the prevention of polymerization in the subsequent distillation column can be effectively carried out by fulfilling the conditions proposed herein.

EXAMPLES

Now, this invention will be described more specifically below with reference to examples. Wherever "ppm" is mentioned in the following examples and comparative examples, it means "ppm (weight)" unless otherwise specified.

The (meth)acrolein concentration was determined by gas chromatography (FID) and the concentrations of acetaldehydes and acetone were both determined by gas chromatography (FID).

Example 1

Acrylic acid was distilled out with a distillation column of 30 mm in inside diameter, equipped in the top part thereof with a distillation tube and a raw material supplying tube, in the bottom part thereof with a kettle, and in the inner part thereof with five sieve trays made of stainless steel (SUS 316) having an opening ratio of 22%. The feed materials used herein were prepared by adding specific aldehydes and ketone shown in the following Tables 1–3 at varying concentrations to glacial acrylic acid (refined acrylic acid). The distillation was performed under the conditions of 100 mmHg of operating pressure and 88° C. of column bottom temperature. As a polymerization inhibitor, phenothiazine was added to and dissolved in glacial acrylic acid in an amount of 100 ppm based on the amount of the vapor of acrylic acid and the resultant solution was fed into the distillation column via the top thereof. The conditions of the operation continued for 8 hours were visually inspected to rate the effect of prevention of polymerization. The test results are shown in Tables 1–3.

TABLE 1

| No. 1- | Acrolein concentration (ppm) | Conditions of polymerization |
| --- | --- | --- |
| 1 (Comparative Example) | 10100 | Flooding occurred within 2 hours of the start and the operation could not be continued any longer. Polymer formed copiously in the column. |
| 2 | 1900 | Polymer formed slightly after 8 hours' stable operation. |
| 3 | 70 | No polymer formed after 8 hours' stable operation. |

TABLE 2

| No. 2- | Acetaldehyde concentration (ppm) | Conditions of polymerization |
| --- | --- | --- |
| 1 (Comparative Example) | 9500 | Flooding occurred within 3 hours of the start and the operation could not be continued any longer. Polymer formed copiously in the column. |
| 2 | 1700 | Polymer formed slightly after 8 hours' stable operation. |
| 3 | 50 | No polymer formed after 8 hours' stable operation |

TABLE 3

| No. 3- | Concentration of pertinent compound (ppm) | | | Condition of polymerization |
| --- | --- | --- | --- | --- |
| | Acetaldehyde | Acrolein | Acetone | |
| 1 (Comparative Example) | 4800 | 4900 | 5100 | Flooding occurred within 1 hour of the start and the operation could not be continued any longer. Polymer formed copiously in the column. |
| 2 | 480 | 490 | 510 | Polymer formed slightly after 8 hours' stable operation. |
| 3 | 30 | 30 | 30 | No polymer formed after 8 hours' stable operation. |

Example 2

Methacrylic acid was distilled out with a distillation column of 30 mm in inside diameter equipped in the top part thereof with a distillation tube and a raw material supplying tube, in the bottom part thereof with a kettle, and in the inner part thereof with five sieve trays made of stainless steel (SUS 316) having an opening ratio of 22%. The feed materials used herein were prepared by adding specific aldehydes and ketone shown in the following Table 4 at varying concentrations to glacial methacrylic acid (refined methacrylic acid). The distillation was performed under the conditions of 100 mmHg of operating pressure and 107° C. of column bottom temperature. As a polymerization inhibitor, phenothiazine was added to and dissolved in glacial acrylic acid in an amount of 100 ppm based on the amount of the vapor of methacrylic acid and the resultant solution was fed into the distillation column via the top thereof. The conditions of the operation continued for 8 hours were visually inspected to rate the effect of prevention of polymerization. The test results are shown in Table 4.

TABLE 4

| No. 4- | Concentration of pertinent compound (ppm) | | | Condition of polymerization |
|---|---|---|---|---|
| | Acetaldehyde | Methacrolein | Acetone | |
| 1 (Comparative Example) | 5200 | 5100 | 4800 | Flooding occurred within 3 hours of the start and the operation could not be continued any longer. Polymer formed copiously in the column. |
| 2 | 520 | 510 | 480 | Polymer formed slightly after 8 hours' stable operation. |
| 3 | 30 | 30 | 30 | No polymer formed after 8 hours' stable operation. |

The polymerization during the course of distillation could be effectively prevented by setting the concentration of specific aldehydes and ketone in the methacrylic acid below a specific level as shown in Table 4.

Example 3

An aqueous acrylic acid solution was distilled with a packed tower equipped in the top part thereof with a distillation tube, a reflux solution supply tube, and a polymerization inhibitor supply tube, in the central part thereof with a raw material supply tube, and in the bottom part thereof with a kettle, a bottoms extracting tube, and an oxygen supply tube.

The aqueous acrylic acid solution subjected to the distillation contained 30 wt. % of water, 5 ppm of acetaldehyde, 70 ppm of acrolein, and 20 ppm of acetone (invariably based on the amount of acrylic acid). It was obtained by causing a reaction mixture gas resulting from catalytic gas phase oxidation of propylene to contact with water thereby giving rise to a mixed solution containing 130 ppm of acetaldehyde, 2500 ppm of acrolein, and 270 ppm of acetone (invariably based on the amount of acrylic acid), feeding the mixed solution into a stripping column (a packed tower maintained under the conditions of 200 mmHg of operating pressure, 70° C. of column top temperature, and 72° C. of bottom temperature), and extracting the effluent from the stripping column. This aqueous acrylic acid solution, after adding a varying compound shown in Table 5 below at a stated concentration, was supplied at a flow volume of 100 ml/hour to the packed tower mentioned above. The distillation, with toluene as a ref luxing medium, was performed under the conditions of 190 mmHg of operating pressure, 50° C. of column top temperature, and 100° C. of bottom temperature.

The refluxing medium, after adding and solving 1.5 ppm of copper dibutyl dithiocarbamate and 10 ppm of phenothiazine each as a polymerization inhibitor, was fed into the column via the top thereof. The aqueous acrylic acid solution, after adding and solving 2 ppm of manganese acetate and 10 ppm of hydroquinone (HQ) (all of them based on the amount of the vapor of acrylic acid), was fed into the column via the raw material supply tube. Through the bottom of the column, oxygen was supplied in an amount of 0.3 vol. % based on the amount of the vapor of acrylic acid.

When the operation was performed under the conditions of No. 5–4 shown in Table 5, the effluent extracted in a stationary state via the bottom of the column was composed of 97.5 wt. % of acrylic acid, 0.02 wt. % of water, not more than the limit of detection (1 ppm) of acetaldehyde, 20 ppm of acrolein, 10 ppm of acetone, and 2.48 wt. % of other components. When the operation was performed under the conditions of No. 4-1 shown in Table 4, the effluent extracted in a stationary state via the bottom of the column was composed of 97.4 wt. % of acrylic acid, 0.02 wt. % of water, 10 ppm of acetaldehyde, 1520 ppm of acrolein, 570 ppm of acetone, and 2.37 wt. % of other components. The reflux medium was used by recycling the effluent oil phase. After 8 hours' operation, the interior of the column was aspirated via the lower part of the column with a vacuum pump having the minimum pressure of $5\times10^{-4}$ Torr at room temperature for 15 hours to dry the interior. Then the weight of the polymer formed in the column was determined to rate the effect of preventing polymerization. The results are shown in Table 5.

TABLE 5

| No. 5- | Concentration based on acrylic acid in aqueous acrylic acid solution (ppm) | | | Amount of polymer formed (g) |
|---|---|---|---|---|
| | Acetaldehyde | Acrolein | Acetone | |
| 1 (Comparative Example) | 500 | 5000 | 1000 | 19.1 |
| 2 | 150 | 1500 | 300 | 4.5 |
| 3 | 35 | 350 | 70 | 0.8 |
| 4 | 5 | 70 | 20 | 0.0 |

It is clearly noted from Table 5 that when the total content of acetaldehydes and acrolein and acetone was not more than 2000 ppm based on the amount of acrylic acid in the aqueous acrylic acid solution (Run Nos. 5-2, 3, and 4 in Table 5), the amounts of polymer formed were smaller by one decimal place than when the total content was 6500 ppm (Run No. 5-1 in Table 5). The amount of polymer formed during the distillation could be repressed substantially to zero when the total content was not more than 500 ppm (Run No. 5-3 in Table 5) ,preferably when the total content was not more than 100 ppm (Run No. 5-4 in Table 5).

When the mixed gas obtained by the catalytic gas phase oxidation of propylene and/or acrolein with a molecular oxygen-containing gas was fed to the acrylic acid collection column to collect an acrylic acid-containing solution and this acrylic acid-containing solution was fed to the distillation column to separate and recover acrylic acid, the polymerization of acrylic acid in the distillation column could be effectively prevented by limiting the total content of aldehydes of 2–4 carbon atoms and acetone in the acrylic acid-containing solution being fed into the distillation column in accordance with the method of this invention. As a result, the apparatus for the distillation of acrylic acid could be operated for a long time.

Further, by simultaneously using molecular oxygen, the polymerization of acrylic acid could be prevented more effectively.

When the mixed gas obtained by the catalytic gas phase oxidation of isobutylene, t-butyl alcohol, and/or methacrolein with a molecular oxygen-containing gas was fed to the methacrylic acid collection column to collect a methacrylic acid-containing solution and this methacrylic acid-containing solution was fed to the distillation column to separate and recover methacrylic acid, the polymerization of methacrylic acid in the distillation column could be effectively prevented by limiting the total content of aldehydes of 2–4 carbon atoms and acetone in the methacrylic acid-containing solution being fed into the distillation column in accordance with the method of this invention. As a result, the apparatus for the distillation of methacrylic acid could be operated for a long time.

Further, by simultaneously using molecular oxygen, the polymerization of methacrylic acid could be prevented more effectively.

The entire disclosure of Japanese Patent Application No.11-093859 filed on Mar. 31, 1999 including specification, claims, drawings and summary are incorporated herein by reference in its entirety.

What is claimed is:

1. A method for refining (meth)acrylic acid, which method comprises the steps of:

feeding a mixed gas including (meth)acrylic acid obtained by gas phase oxidation into a collection column for collecting it as a (meth)acrylic acid-containing solution; and feeding the (meth)acrylic acid-containing solution into a distillation column while maintaining a total concentration of aldehydes of 2–4 carbon atoms and acetone at a level of not more than 2000 ppm based on the amount of (meth)acrylic acid in the (meth)acrylic acid solution, wherein (meth)acrylic acid is separated or recovered and polymerization of acrylic acid is prevented.

2. A method according claim 1, wherein in the step of feeding a mixed gas to the collection column the mixed gas results from catalytic gas phase oxidation of a raw material gas containing propylene and/or acrolein with a molecular oxygen-containing gas or from catalytic gas phase oxidation of a raw material gas containing at least one compound selected from the group consisting of isobutylene, t-butyl alcohol, methacrolein, and a mixture thereof with a molecular oxygen-containing gas and the (meth)acrylic acid-containing solution is collected in the collection column from the gas.

3. A method according to claim 2, wherein the total concentration of aldehydes of 2–4 carbon atoms and acetone is maintained at a level of not more than 500 ppm based on the amount of (meth)acrylic acid.

4. A method according to claim 2 further containing (meth)acrolein wherein the concentration of the (meth)acrolein is not more than 100 ppm based on the amount of (meth)acrylic acid.

5. A method according to claim 4, wherein the concentration of the (meth)acrolein is not more than 50 ppm based on the amount of (meth)acrylic acid.

6. A method according to claim 2 further comprising the step of feeding the (meth)acrylic acid-containing solution into a stripping column in advance of the step of feeding the (meth)acrylic acid-containing solution into the distillation column and then feeding the solution extracted from the stripping column through the bottom of the stripping column into the distillation column for separation or recovery of (meth)acrylic acid.

7. A method according to claim 2 further comprising the step of adding a polymerization inhibitor when the (meth)acrylic acid-containing solution is fed to the distillation column, the polymerization inhibitor being at least one compound selected from the group consisting of hydroquinone, methoquinone, phenothiazine, a copper salt compound, a manganese salt compound, a p-phenylene diamine compound, a N-oxyl compound, a nitroso compound, a urea compound, a thiourea compound, and a mixture thereof.

8. A method according to claim 7, wherein the inhibitor is at least one compound selected from the group consisting of hydroquinone, methoquinone, phenothiazine, a copper salt compound, a manganese salt compound, a N-oxyl compound, a nitroso compound, and a mixture thereof.

9. A method according to claim 8, wherein the inhibitor is at least one compound selected from the group consisting of phenotiazine, a N-oxyl compound, and a mixture thereof.

10. A method according to claim 7, wherein an amount of the inhibitor is in the range of 1 to 1000 ppm based on the amount of a vapor of (meth)acrylic acid.

11. A method according to claim 10, wherein the amount of the inhibitor is in the range of 5 to 500 ppm based on the amount of the vapor of (meth)acrylic acid.

12. A method according to claim 1 further comprising the step of distilling the (meth)acrylic acid-containing solution in the presence of a molecular oxygen.

13. A method according to claim 12, wherein an amount of the molecular oxygen is in the range of 0.1 to 1% by volume based on the amount of a vapor of (meth)acrylic acid in the distillation column.

14. The method of claim 1 wherein the step of maintaining the total concentration of aldehydes of 2–4 carbon atoms and acetone is performed by the step of:

increasing a rate of conversion of acrolein in the gas phase oxidation.

15. The method of claim 1 wherein the step of maintaining the total concentration of aldehydes of 2–4 carbon atoms and acetone is performed by the step of:

elevating a temperature in the collection column.

* * * * *